(12) United States Patent
Yang et al.

(10) Patent No.: US 9,672,611 B2
(45) Date of Patent: Jun. 6, 2017

(54) PATTERN ANALYSIS METHOD OF A SEMICONDUCTOR DEVICE

(71) Applicant: SAMSUNG ELECTRONICS CO., LTD., Suwon-si, Gyeonggi-do (KR)

(72) Inventors: Kiho Yang, Gyeonggi-do (KR); Kaiyuan Chi, Gyeonggi-do (KR); Seunghune Yang, Seoul (KR); Sibo Cai, Gyeonggi-do (KR)

(73) Assignee: Samsung Electronics Co., Ltd., Suwon-Si, Gyeonggi-Do (KR)

( * ) Notice: Subject to any disclaimer, the term of this patent is extended or adjusted under 35 U.S.C. 154(b) by 39 days.

(21) Appl. No.: 14/693,914

(22) Filed: Apr. 23, 2015

(65) Prior Publication Data

US 2016/0071261 A1    Mar. 10, 2016

(30) Foreign Application Priority Data

Sep. 5, 2014   (KR) .................. 10-2014-0118917

(51) Int. Cl.
*G06K 9/00* (2006.01)
*G06T 7/00* (2017.01)
(Continued)

(52) U.S. Cl.
CPC ............ *G06T 7/001* (2013.01); *G01N 23/20* (2013.01); *H01L 22/12* (2013.01);
(Continued)

(58) Field of Classification Search
CPC .......... G06T 7/001; G06T 2207/30148; G06T 2207/10061; H01L 22/12; G01N 23/20;
(Continued)

(56) References Cited

U.S. PATENT DOCUMENTS 7,485,858 B1 * 2/2009 Obara .................. H01J 37/222
250/306
8,090,186 B2   1/2012 Nagano
(Continued)

FOREIGN PATENT DOCUMENTS

JP    2003174066    6/2003
JP    2010135416    6/2010
(Continued)

*Primary Examiner* — Aaron W Carter
(74) *Attorney, Agent, or Firm* — F. Chau & Associates, LLC

(57) ABSTRACT

A pattern analysis method of a semiconductor device includes extracting a contour image of material layer patterns formed on a wafer, calculating an individual density value (DV) representing an area difference between the contour image and a target layout image, scoring the material layer patterns on the wafer using the individual DV, identifying a failure pattern among the scored material layer patterns, calculating coordinates of the identified failure pattern and displaying the coordinates on a critical dimension-scanning electron microscopy (CD-SEM) image, inputting a reference DV in the computer and automatically sorting the material layer patterns into material layer patterns having a hotspot and material layer patterns not having a hotspot, and reviewing the sorted material layer patterns having the hotspot.

18 Claims, 11 Drawing Sheets

(51) Int. Cl.
  *H01L 21/66*     (2006.01)
  *G01N 23/20*     (2006.01)
  *H01J 37/22*     (2006.01)
  *H01J 37/28*     (2006.01)
(52) U.S. Cl.
  CPC ............. *G06T 2207/10061* (2013.01); *G06T 2207/30148* (2013.01); *H01J 37/222* (2013.01); *H01J 37/28* (2013.01); *H01J 2237/24592* (2013.01); *H01J 2237/2816* (2013.01); *H01J 2237/2817* (2013.01)
(58) Field of Classification Search
  CPC ............... H01J 37/222; H01J 37/28; H01J 2237/24592; H01J 2237/2817; H01J 2237/2816
  See application file for complete search history.

(56) References Cited

U.S. PATENT DOCUMENTS

| | | | |
|---|---|---|---|
| 8,532,395 B2 | 9/2013 | Mitsui | |
| 2003/0107736 A1 | 6/2003 | Fujimoto | |
| 2007/0057177 A1* | 3/2007 | Kim | H01J 49/401 250/287 |
| 2007/0186206 A1* | 8/2007 | Abrams | G03F 1/144 716/52 |
| 2008/0232671 A1* | 9/2008 | Asano | G03F 1/0092 382/144 |
| 2009/0007052 A1* | 1/2009 | Yang | G06F 17/5081 716/53 |
| 2009/0123058 A1* | 5/2009 | Ito | G03F 1/0092 382/144 |
| 2009/0136121 A1* | 5/2009 | Nakagaki | G06T 7/0006 382/149 |
| 2009/0231424 A1* | 9/2009 | Honda | G06T 7/0006 348/87 |
| 2010/0084667 A1* | 4/2010 | Mcfadden | F21K 9/00 257/88 |
| 2010/0131915 A1* | 5/2010 | Hirabayashi | G03F 1/144 716/50 |
| 2012/0121160 A1* | 5/2012 | Matsuoka | H01J 37/28 382/145 |
| 2013/0064442 A1* | 3/2013 | Chang | G06T 7/001 382/149 |
| 2013/0174102 A1* | 7/2013 | Leu | G05B 19/41875 716/52 |
| 2015/0110383 A1 | 4/2015 | Yang et al. | |
| 2015/0110384 A1* | 4/2015 | Luoh | G06T 7/0006 382/149 |
| 2016/0071261 A1* | 3/2016 | Yang | H01L 22/12 382/149 |

FOREIGN PATENT DOCUMENTS

| | | |
|---|---|---|
| JP | 2011247957 | 12/2011 |
| KR | 1020150045783 | 4/2015 |

* cited by examiner

PATTERN ANALYSIS METHOD OF A SEMICONDUCTOR DEVICE

CROSS-REFERENCE TO RELATED APPLICATION

This application claims priority under 35 U.S.C. §119 to Korean Patent Application No. 10-2014-0118917 filed on Sep. 5, 2014, the disclosure of which is incorporated by reference herein in its entirety.

TECHNICAL FIELD

Exemplary embodiments of the inventive concept relate to a pattern analysis method which detects failure factors (e.g., hotspots) on a wafer.

DISCUSSION OF THE RELATED ART

Patterns (or, structures) of various conductive or insulating layers of a semiconductor device are integrated on a wafer through a photo-etching process. The photo-etching process may include patterning a mask, exposing a layer, and developing the layer. However, various failure factors may be generated during the photo-etching process. These various failure factors may include the formation of a bridge, in which adjacent patterns on the wafer are undesirably connected, a pinch, in which a pattern has a width equal to or smaller than a critical dimension (CD), or an edge placement error (EPE), in which an end region of the pattern is too small.

SUMMARY

In accordance with an exemplary embodiment of the inventive concept, a pattern analysis method of a semiconductor device includes extracting a contour image of material layer patterns formed on a wafer, calculating an individual density value (DV) indicating area difference between the contour image and a target layout image, scoring the material layer patterns formed on the wafer using the individual DV, identifying a failure pattern among the scored material layer patterns, calculating coordinates of the identified failure pattern and displaying the coordinates on a critical dimension-scanning electron microscopy (CD-SEM) image, inputting a reference DV in the computer and automatically sorting the material layer patterns into material layer patterns having a hotspot and material layer patterns not having a hotspot, and reviewing the material layer patterns having the hotspot.

In accordance with an exemplary embodiment of the inventive concept, the contour image is extracted with respect to end regions of the material layer patterns.

In accordance with an exemplary embodiment of the inventive concept, the target layout image includes an original design target layout, a smoothing target layout, or a simulation target layout.

In accordance with an exemplary embodiment of the inventive concept, the individual (DV) is calculated through the following Equation:

$$DV = \frac{\text{Area\_difference}}{\text{Area}(SEMunit)} = \frac{\text{Boolean\_operation}(XOR)}{\text{Area}(SEMunit)} =$$

$$\frac{[\text{Area}(SEMunit) - \text{Area}(SEMsilhouette \cap \text{Target})] + [\text{Area}(\text{Target}) - \text{area}(SEMsilhouette \cap \text{Target})]}{\text{Area}(SEMunit)}.$$

In accordance with an exemplary embodiment of the inventive concept, a failure pattern is identified when an area matched between the contour image and the target layout image is less than a predetermined threshold.

In accordance with an exemplary embodiment of the inventive concept, the identified failure pattern includes a "bridge," a "pinch," or an "Edge Placement Error (EPE)."

In accordance with an exemplary embodiment of the inventive concept, the inputting of the reference DV and the automatically sorting of the material layer patterns on the wafer into those having a hotspot and those not having a hotspot includes inputting a DV data file, a pinch/bridge/Edge Placement Error (EPE) data file, an image data file, and a threshold value for sorting the DV into a review tool installed in the computer, and sorting the material layer patterns on the wafer into a "BAD" list which includes material layer patterns having a hotspot, a "GOOD" list which includes material layer patterns not having a hotspot, and a "VAGUE" list which includes material layer patterns not having a hotspot, according to the input DV data file, pinch/bridge/EPE data file, image data file, and threshold value for sorting the DV.

In accordance with an exemplary embodiment of the inventive concept, each of the lists includes a unique identifier (ID) of each material layer pattern and a DV corresponding to the ID.

In accordance with an exemplary embodiment of the inventive concept, when selecting an ID included in each of the lists, a CD-SEM image of a material layer pattern corresponding to the selected ID is displayed, and a location of the hotspot, the contour image, and the target layout image of the selected ID are simultaneously displayed on the corresponding CD-SEM image.

In accordance with an exemplary embodiment of the inventive concept, the material layer patterns sorted as having a hotspot include material layer patterns having an actual hotspot and material layer patterns having a potential hotspot in which a failure is able to be generated.

In accordance with an exemplary embodiment of the inventive concept, the reviewing includes visually reviewing the material layer patterns having the actual hotspot and the material layer patterns having the potential hotspot.

In accordance with an exemplary embodiment of the inventive concept, a critical dimension (CD) value of each material layer pattern displayed on the CD-SEM image is measured and displayed in real-time.

In accordance with an exemplary embodiment of the inventive concept, a pattern analysis method of a semiconductor device includes calculating a DV representing an area difference between a contour image of the material layer patterns and a target layout image, using a computer, inputting a reference DV to be compared with the calculated DV of the material layer patterns and automatically detecting a hotspot of the material layer patterns, using the computer, displaying the detected hotspot on a CD-SEM image, using the computer, and performing a visual inspection of the displayed hotspot on the CD-SEM image.

In accordance with an exemplary embodiment of the inventive concept, an optical proximity correction (OPC) is performed after performing the visual inspection.

In accordance with an exemplary embodiment of the inventive concept, the CD-SEM image includes a two-dimensional CD-SEM image or a three-dimensional CD-SEM image.

In accordance with an exemplary embodiment of the inventive concept, the hotspot is a failure point.

In accordance with an exemplary embodiment of the inventive concept, a pattern analysis method of a semiconductor device includes obtaining a contour image of material layer patterns on a wafer, overlapping the contour image and a target layout image, obtaining a DV representing an area difference between the contour image and the target layout image, scoring the material layer patterns based on the DV, sorting the scored material layer patterns into material layer patterns that include a failure pattern, which is indicative of a hotspot, and material layer patterns that do not include the failure pattern, calculating coordinates on the wafer for the failure pattern and displaying the calculated coordinates on an image, automatically detecting a hotspot by applying a reference DV to the material layer patterns that include the failure pattern, and reviewing the automatically detected hotspot.

In accordance with an exemplary embodiment of the inventive concept, the image includes a two-dimensional critical dimension-scanning electron microscopy (CD-SEM) image or a three-dimensional CD-SEM image.

In accordance with an exemplary embodiment of the inventive concept, an optical proximity correction (OPC) is performed after reviewing the automatically detected hotspot.

In accordance with an exemplary embodiment of the inventive concept, the DV is calculated through the following Equation:

$$DV = \frac{\text{Area\_difference}}{\text{Area}(SEMunit)} = \frac{\text{Boolean\_operation}(XOR)}{\text{Area}(SEMunit)} =$$
$$\frac{[\text{Area}(SEMunit) - \text{Area}(SEMsilhouette \cap Target)] +}{[\text{Area}(Target) - \text{area}(SEMsilhouette \cap Target)]}.$$
$$\frac{}{\text{Area}(SEMunit)}.$$

BRIEF DESCRIPTION OF THE DRAWINGS

The foregoing and other features of the inventive concept will become more apparent by describing in detail exemplary embodiments thereof with reference to the accompanying drawings. In the drawings.

DETAILED DESCRIPTION OF THE EMBODIMENTS

Exemplary embodiments of the inventive concept will now be described more fully with reference to the accompanying drawings. The invention may, however, be embodied in many different forms and should not be construed as being limited to the exemplary embodiments set forth herein.

As used herein, the singular forms "a," "an," and "the," are intended to include the plural forms as well, unless the context clearly indicates otherwise.

Exemplary embodiments are described herein with reference to cross-sectional illustrations that are schematic illustrations of idealized embodiments (and intermediate structures). As such, variations from the shapes of the illustrations as a result, for example, of manufacturing techniques and/or tolerances, may be expected. For example, the exemplary embodiments should not be construed as limited to the particular shapes of regions illustrated herein but may include deviations in shapes that result, for example, from manufacturing. For example, an implanted region illustrated as a rectangle may, typically, have rounded or curved features and/or a gradient of implant concentration at its edges rather than a binary change from an implanted to a non-implanted region. In addition, a buried region formed by implantation may result in some implantation in the region between the buried region and the surface through which the implantation takes place. The regions illustrated in the figures are schematic in nature and their shapes are not intended to illustrate the actual shape of a region of a device and are not intended to limit the scope of the present inventive concept.

Like numbers may refer to like elements throughout the specification and drawings.

Figure 1A:
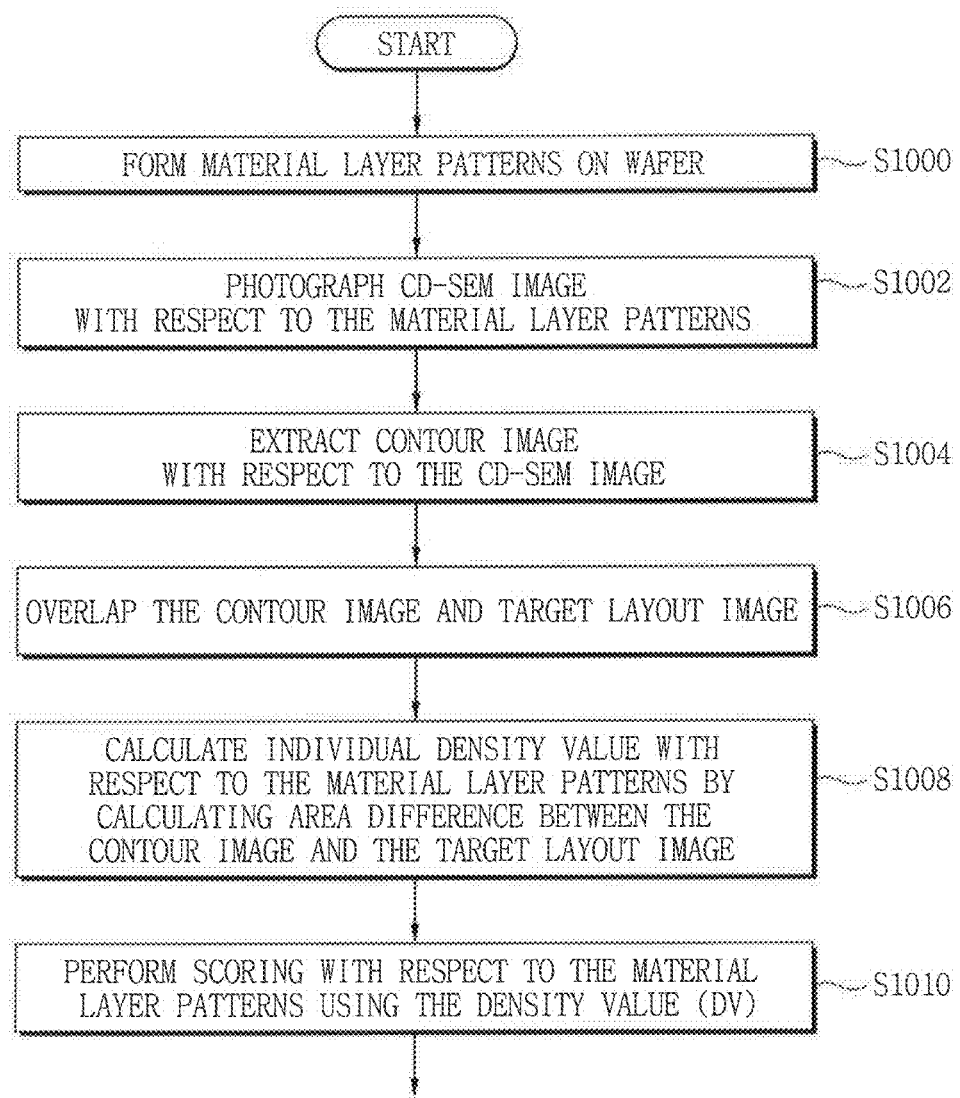
FIGS. 1A and 1B are flow charts illustrating a pattern analysis method of a semiconductor device in accordance with an exemplary embodiment of the inventive concept.
Figure 1B:
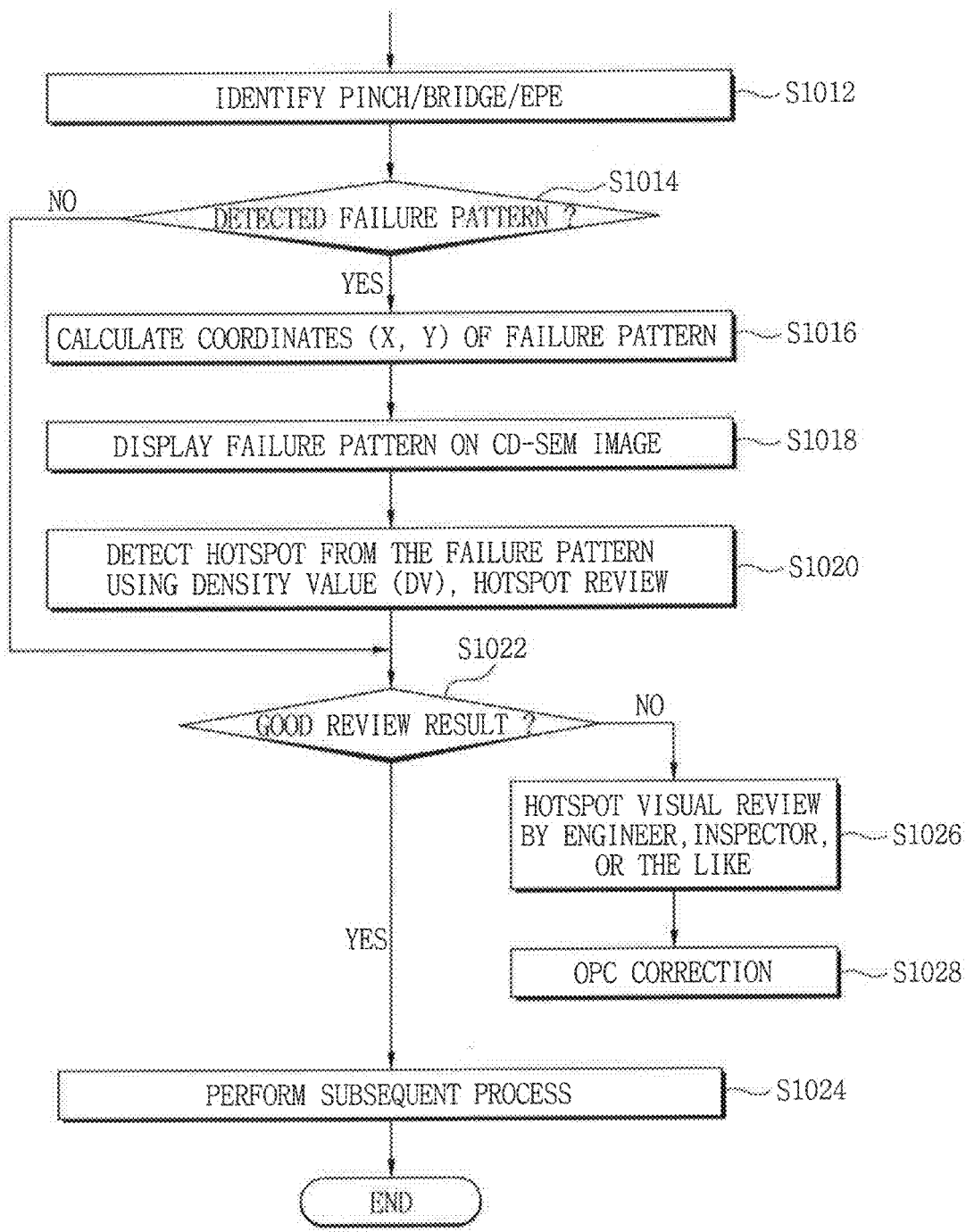

FIGS. 1A and 1B are flow charts illustrating a pattern analysis method of a semiconductor device in accordance with an exemplary embodiment of the inventive concept.

Figure 2:
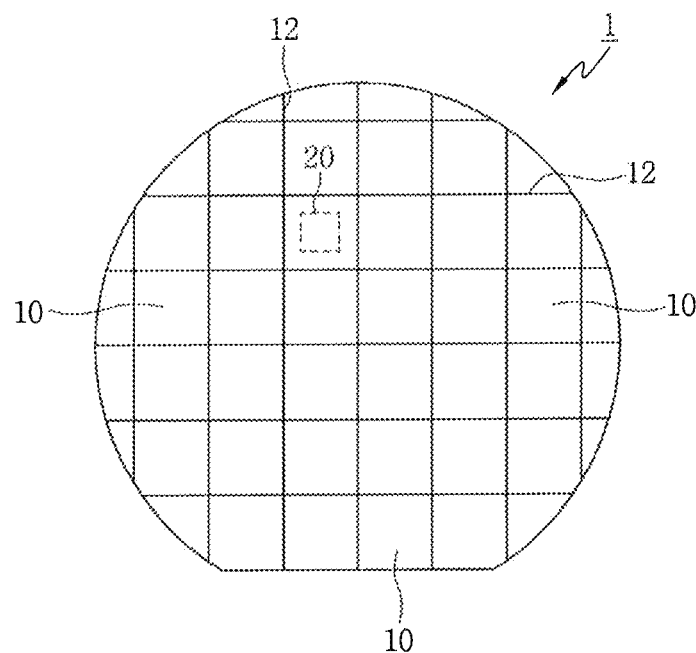
FIG. 2 shows a wafer applied to the methods of FIGS. 1A and 1B.

FIG. 2 shows a wafer 1 applied to the methods of FIGS. 1A and 1B.

Figure 3:
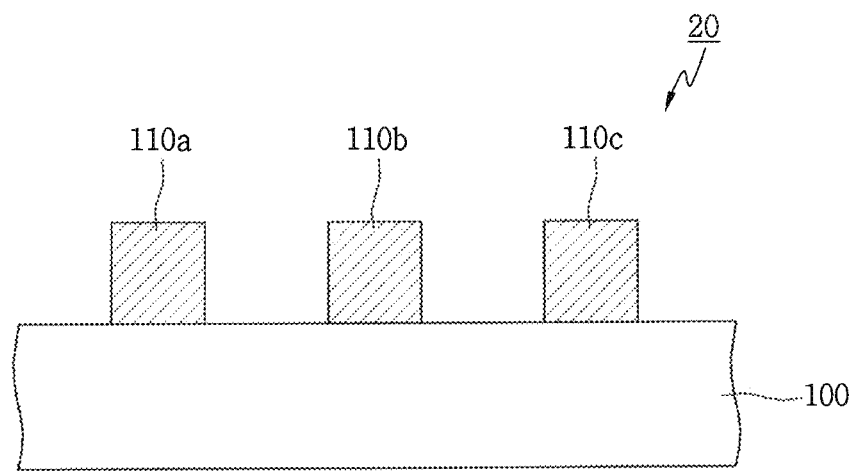
FIG. 3 is a cross-sectional view with respect to a part of the wafer shown in FIG. 2.

FIG. 3 is a cross-sectional view with respect to a part 20 of the wafer 1 shown in FIG. 2.

Figure 4:
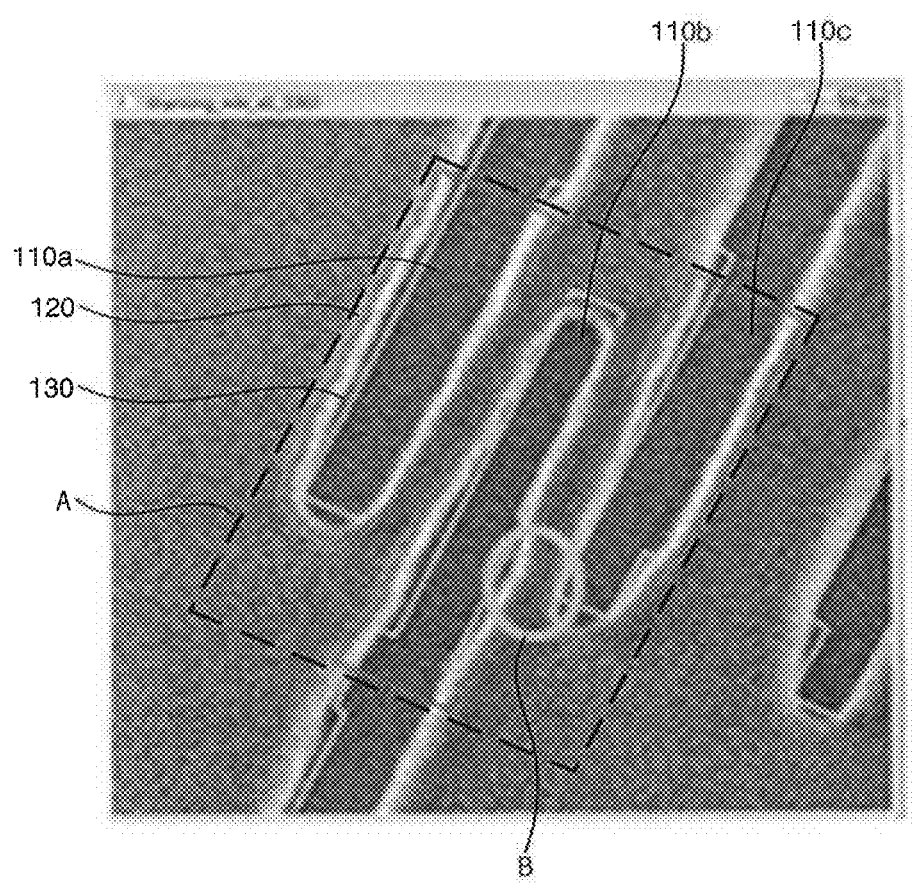
FIG. 4 is an image, in which a contour image overlaps a target layout image, with respect to the part of the wafer shown in FIG. 2.

FIG. 4 is a critical dimension-scanning electron microscopy (CD-SEM) image, in which a contour image 120 overlaps a target layout image 130, with respect to the part 20 of the wafer 1 shown in FIG. 2.

Figure 5:
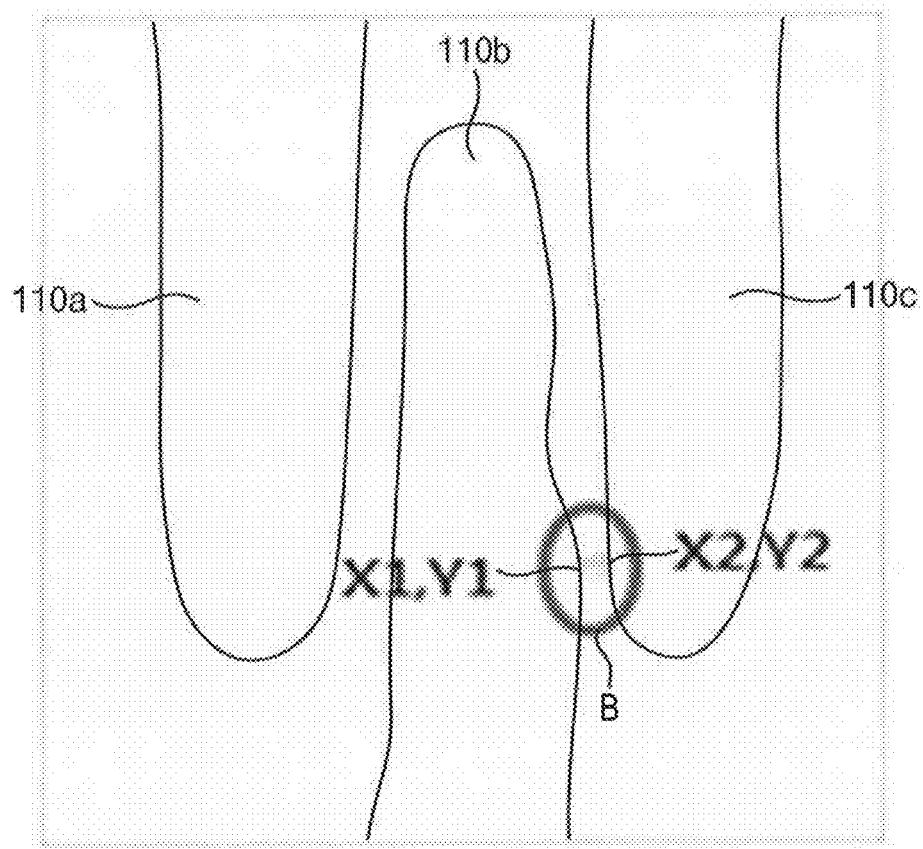
FIG. 5 shows two-dimensional planar coordinates of a failure pattern shown on the overlapping image in FIG. 4.

FIG. 5 shows planar coordinates of a failure pattern B shown on the overlapping image in FIG. 4.

Figure 6:
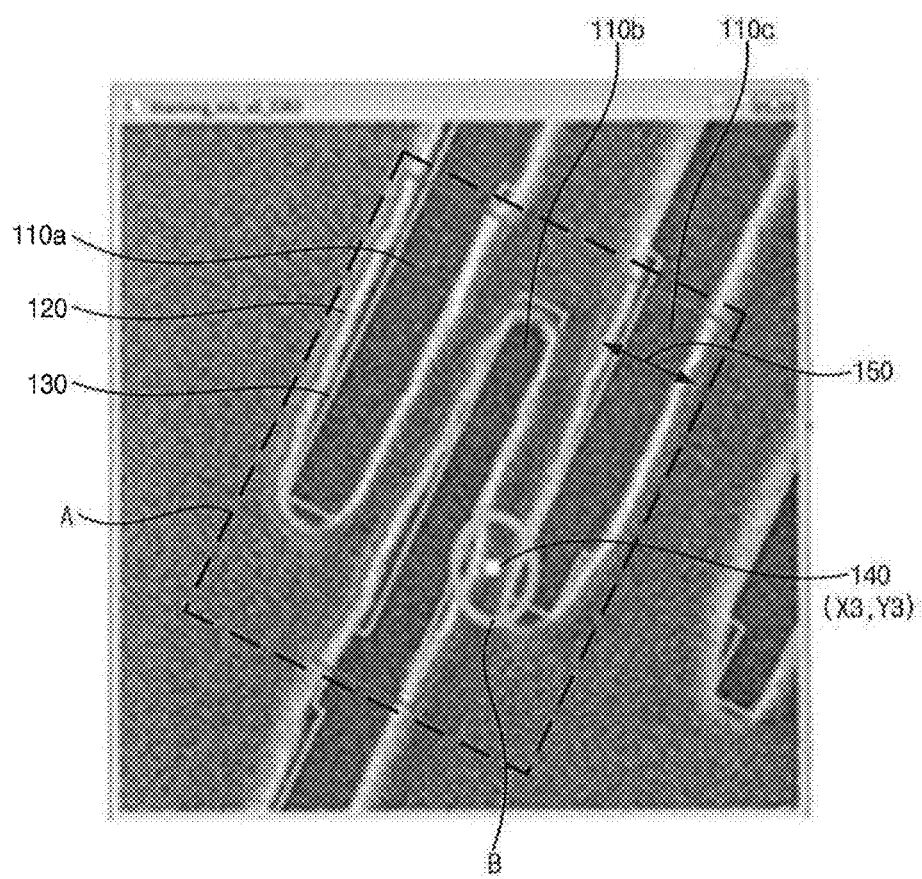
FIG. 6 shows a critical dimension-scanning electron microscopy (CD-SEM) image in which a hotspot is displayed in a spot shape.

FIG. 6 shows a CD-SEM image in which a hotspot 140 is displayed in a spot shape.

Figure 7:
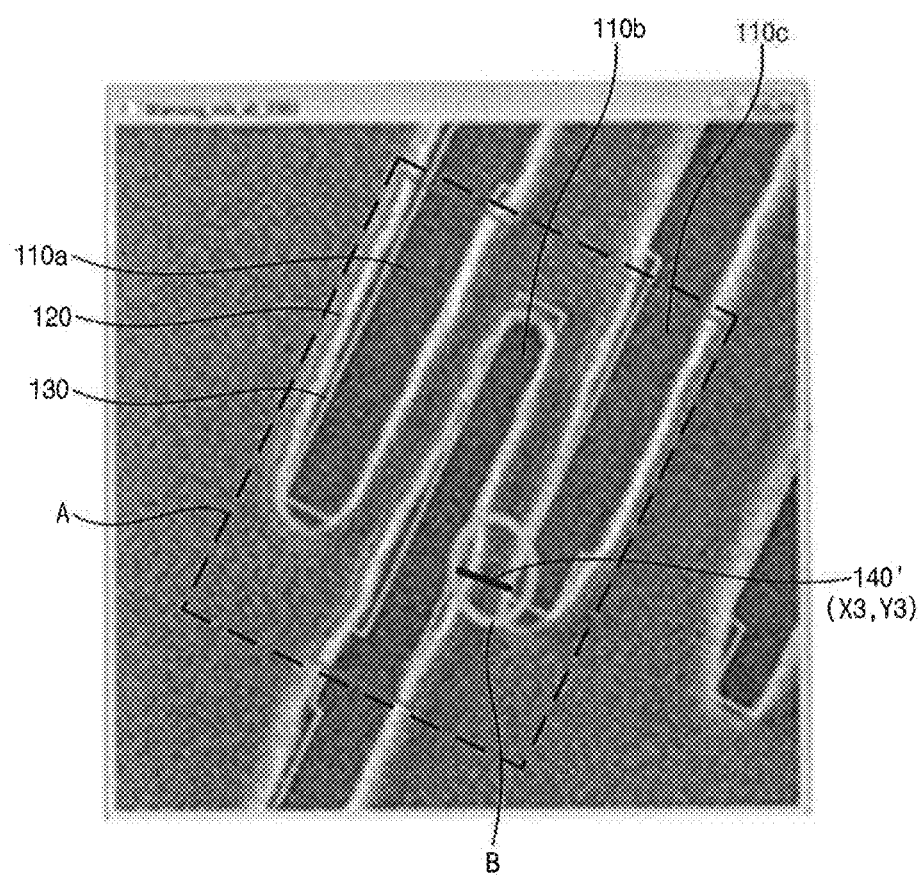
FIG. 7 shows a CD-SEM image in which a hotspot is displayed in a line shape.

FIG. 7 shows a CD-SEM image in which a hotspot 140' is displayed in a line shape.

Figure 8:
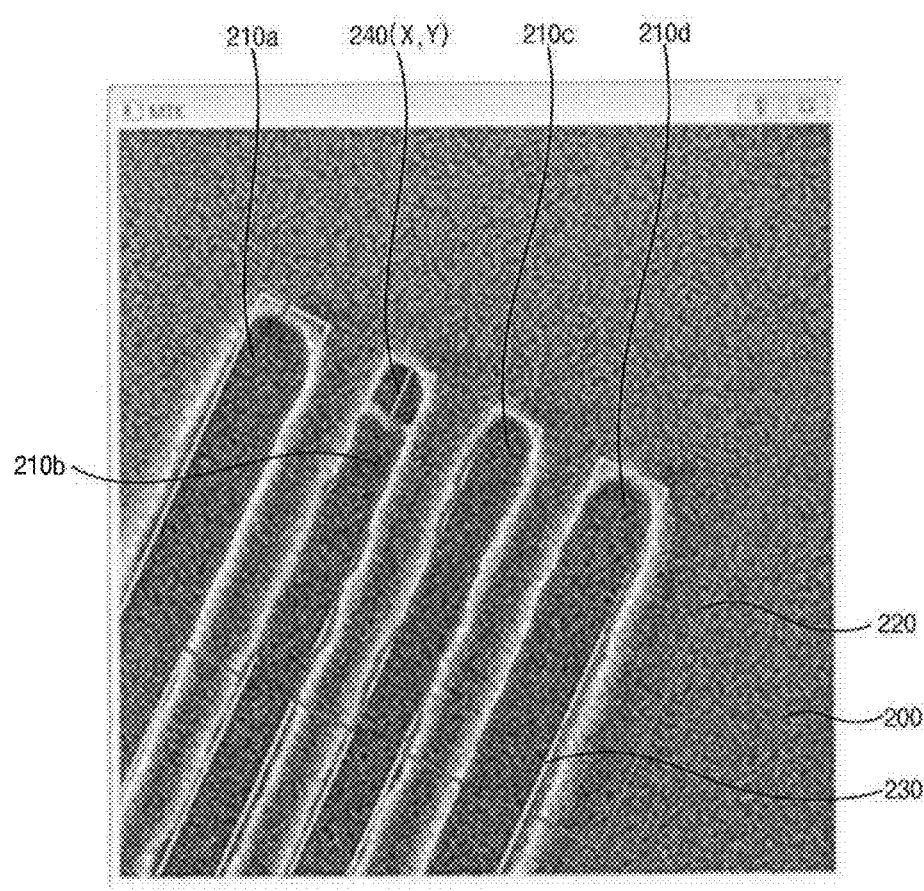
FIG. 8 shows a CD-SEM image in which an edge placement error (EPE) is generated in another shape of a hotspot.

FIG. 8 shows a CD-SEM image in which an edge placement error (EPE) is generated in another shape of a hotspot 240.

The pattern analysis method of the semiconductor device will be described with reference to FIGS. 1A, 1B, and 2 to 8.

Referring to FIGS. 1A, 1B, 2, and 3 in operation S1000, material layer patterns 110a, 110b, and 110c may be formed on the wafer 1 shown in FIG. 2.

The wafer 1 may include a plurality of chip regions 10 which are separated by scribe lines 12. A chip region 10 may be a region in which a semiconductor device is formed.

The material layer patterns 110a, 110b, and 110c may be formed on an underlayer 100 of the wafer 1. The material layer patterns 110a, 110b, and 110c may include various material layer patterns such as a photoresist pattern, a conductive layer pattern for a path of an electrical signal, an insulating layer which insulates the conductive layer pattern from another adjacent conductive layer pattern, etc. The underlayer 100 may include a semiconductor layer, an insulating layer, a conductive layer, a hard mask layer, etc.

Factors which cause a failure of the semiconductor device, such as a bridge connecting one of the material layer patterns 110a, 110b, or 110c with another material layer pattern, a pinch in which a width of each material layer pattern 110a, 110b, and 110c is equal to or smaller than a critical dimension (CD), an edge placement error (EPE) in which one or more end regions of the material layer patterns 110a, 110b, and 110c are too small, and/or the like, which are generated when forming the material layer patterns 110a, 110b, and 110c, may be a hotspot.

In operation S1002, a CD-SEM image may be photographed with respect to the material layer patterns 110a, 110b, and 110c on the wafer 1.

Referring to FIG. 4, the material layer patterns 110a, 110b, and 110c may include a photoresist pattern which serves as a self-aligned etching mask to selectively etch the underlayer 100, a conductive layer pattern selectively etched by the photoresist pattern, or an insulating layer pattern. When the material layer patterns 110a, 110b, and 110c are photoresist patterns, an exposure light source is incident on a photo mask formed along a pre-designed target layout and then a photoresist layer deposited on the underlayer 100 is selectively exposed. The exposed photoresist layer is developed and then the above-described photoresist patterns are formed. For example, as the underlayer 100 is selectively etched using the developed photoresist patterns 110a, 110b, and 110c as self-aligned etching masks, a photo-etching process is completed.

For example, the material layer patterns 110a, 110b, and 110c may be a conductive or insulating layer pattern which is selectively etched by the photoresist patterns.

However, due to lack of a process margin or a limit of resolution caused by high integration of the semiconductor device, various hotspots such as a bridge, a pinch, an EPE, or the like may be generated when forming the material layer pattern 110a, 110b, and 110c.

Thus, an exemplary embodiment of the inventive concept may detect hotspots which may be generated among the material layer patterns 110a, 110b, and 110c, and perform an optical proximity correction (OPC) as necessary.

In operation S1004, a contour image 120 may be extracted with respect to the material layer patterns 110a, 110b, and 110c in the CD-SEM image shown in FIG. 4.

The contour image 120 may not be extracted with respect to an entire region of the material layer patterns 110a, 110b, and 110c, and may be extracted only with respect to end regions as shown in FIG. 4. The reason why the contour image 120 is extracted only with respect to a part (e.g., the end regions) of the material layer patterns 110a, 110b, and 110c instead of the entire regions of the material layer patterns 110a, 110b, and 110c is because hotspots have a high probability of being generated in the end regions.

The contour image 120 may be extracted using a CD-SEM measurement device. For example, a variety of CD-SEM measurement devices may be used to extract the contour image 120.

The contour image 120 may be stored as a graphic database system (GDS) type file. An application program using the GDS file may display and generate an image file. A variety of images and image types may be displayed in such an application program.

In operation S1006, a target layout image 130 may overlap a contour image 120 as shown in FIG. 4.

The contour image 120 is an image which substantially shows a silhouette with respect to the material layer patterns 110a, 110b, and 110c, and the target layout image 130 is an image to be implemented as an ideal material layer pattern. For example, when overlapping the two images 120 and 130, an area difference is generated between the two images 120 and 130 as shown in FIG. 4.

The target layout image 130 may also be provided as the GDS type file. The target layout image 130 may include an original design target layout, a smoothing target layout, or a simulation target layout.

In operation S1008, a density value (DV) may be calculated for each of the material layer patterns 110a, 110b, and 110c by calculating a difference of an overlapping area between the contour image 120 and the target layout image 130. For example, a DV may be calculated for the material layer pattern 110a by calculating a difference of an overlapping area between the contour image 120 and the target layout image 130. Also, a DV may be calculated for the material layer pattern 110b by calculating a difference of an overlapping area between the contour image 120 and the target layout image 130.

The DV is calculated by a following Equation 1.

$$DV = \frac{\text{Area\_difference}}{\text{Area}(SEMunit)} = \frac{\text{Boolean\_operation}(XOR)}{\text{Area}(SEMunit)} = \\ \frac{[\text{Area}(SEMunit) - \text{Area}(SEMsilhouette \cap \text{Target})] + [\text{Area}(\text{Target}) - \text{area}(SEMsilhouette \cap \text{Target})]}{\text{Area}(SEMunit)}$$

Equation 1

Calculation of the difference of the overlapping area between the contour image 120 and the target layout image 130 is accomplished with respect to end regions of the material layer patterns 110a, 110b, and 110c illustrated as a reference mark A in FIG. 4. The Area(SEMunit) denotes an area of the SEM unit region, the Area(SEMsilhouette) denotes an area of the silhouette of the contour image 120, and the Area(Target) denotes an area of the target layout image 130.

When a value of the DV is small, a matching area between the contour image and the target layout image is large. On the other hand, when the value of the DV is large, the matching area between the contour image and the target layout image is small. Thus, a probability of hotspot generation is increased when the value of the DV is increased. In other words, when the DV goes above a predetermined threshold, the matching area may be small and thus a hotspot may be present.

In operation S1010, a scoring process, which scores the material layer patterns formed on the wafer 1, may be performed using the DV. The DV indicates the difference of the overlapping area between the contour image 120 and the target layout image 130.

A region of the reference mark A in FIG. 4 which defines the end regions of the material layer patterns 110a, 110b, and 110c may be a unit region to calculate the DV. For example, several hundreds to several thousands of unit regions, such as the region of the reference mark A, may be included in the wafer 1. The DV is calculated with respect to each of the plurality of unit regions shown on the wafer 1 and the material layer patterns are scored using the calculated DV.

In operation S1012, failure factors such as a "pinch," a "bridge," an "EPE," or the like may be identified with respect to the scored material layer patterns.

The failure factors (e.g., the pinch, the bridge, and the EPE) might not always be generated in proportion to the DV. A large DV may not be identified as the failure factor. On the other hand, a small DV may be identified as the failure factor.

For example, the failure patterns, classified as the "pinch," the "bridge," the "EPE," and/or the like, may include all failure patterns which are not only a pattern in which a failure is clearly generated from the material layer patterns as the bridge, the pinch, the EPE, or the like, but also a pattern in which a failure is not clearly generated but may lead to failure generation.

In operation S1014, when a failure pattern is detected by identifying a pinch, a bridge, or an EPE in operation S1012, the failure pattern may be checked (or, marked).

When the failure pattern (e.g., the pinch, the bridge, or the EPE) is not detected, the wafer 1 including a "GOOD" pattern proceeds to subsequent operation S1022.

When the failure pattern (e.g., the pinch, the bridge, or the EPE) is detected, the wafer 1 proceeds to operation S1016 and coordinates of a point located at the detected failure pattern are calculated.

FIG. 4 shows a failure pattern B identified in operation S1012.

Referring to FIG. 4, the failure pattern B may be a bridge generated between a right side of a material layer pattern 110b and a left end region of a material layer pattern 110c. Although the bridge is not generated by substantially connecting the material layer patterns 110b and 110c, the failure pattern is identified almost the same as a bridge generated by connecting the material layer patterns 110b and 110c.

In operation S1016, original planar coordinates (X, Y) on a wafer may be calculated with respect to the failure pattern B detected as a bridge-type as shown in FIG. 5.

A bridge, which is one of various failure factors generated on the wafer, may not be a failure factor independently generated in one pattern but may be a failure factor generated between two adjacent patterns. For example, bridge generated points (X1, Y1) and (X2, Y2), in which the bridge B is generated between the material layer pattern 110b and 110c, are simultaneously calculated.

Coordinate calculation with respect to the bridge B may be calculated using a calibration program.

In operation S1018, the failure pattern B may be displayed on the CD-SEM image in which the contour image 120 overlaps the target layout image 130.

The failure pattern B may be displayed in a spot shape 140 (X3, Y3) which may be a middle point between the coordinates (X1, Y1) of the material layer pattern 110b and the coordinates (X2, Y2) of the material layer pattern 110c at which a bridge was generated, as shown in FIG. 6.

Further, the failure pattern B may be displayed in a line shape 140' (X3, Y3) which may be a connection between the coordinates (X1, Y1) of the material layer pattern 110b and the coordinates (X2, Y2) of the material layer pattern 110c at which a bridge was generated, as shown in FIG. 7.

FIG. 8 shows a CD-SEM image in which a shape of a failure pattern 240 is displayed.

The CD-SEM image shown in FIG. 8 may include a contour image 220, a target layout image 230, and a failure pattern 240 with respect to material layer patterns 210a, 210b, 210c, and 210d on an underlayer 200.

The failure pattern 240 may be an EPE failure in which an end region of the pattern 210b is entirely short. As the failure pattern 240 is generated in the one pattern 210b, coordinates (X, Y) may be displayed. The CD-SEM image including the failure pattern B 240 may include a focus energy matrix (FEM) image or a single image as shown in FIGS. 6, 7, and 8.

In operation S1020, a hotspot may be detected from the failure patterns and the detected hotspot is reviewed through the CD-SEM image.

The review with respect to the hotspot may be accomplished using a review tool installed in a computer. The review tool may be based on a C++ program, and may include input items of the following: input items for DV data files, input items for pinch/bridge/EPE data files, input items for image data files, and input items of threshold values for sorting DVs.

When the input items for DV data files, input items for pinch/bridge/EPE data files, input items for image data files, and input items of threshold values for sorting DVs are input to the review tool, all scored material layer patterns (e.g., good patterns and failure patterns) on a wafer are sorted into "GOOD," "VAGUE," and "BAD" lists.

The "GOOD" and the "VAGUE" lists include material layer patterns not having hotspots and the "BAD" list denotes material layer patterns having a clear hotspot. Although the material layer patterns may be sorted into a "VAGUE" list are not sorted as having a hotspot, they may have a potential hotspot region in which a failure may be generated.

Reference DVs are input to the input items of threshold values for sorting DVs to sort hotspot patterns among the scored material layer patterns on the wafer. The reference DVs may be arbitrarily assigned and input by an engineer, inspector, or the like.

The material layer patterns may be sorted as having or not having a hotspot according to the threshold values input by an engineer, inspector, or the like. A good pattern, which was not identified as a failure pattern in operation 1012, may be sorted into a "VAGUE" or "BAD" list by the threshold values input by the engineer, inspector, or the like. On the other hand, a failure pattern which was identified as a bridge, a pinch, an EPE or the like in operation 1012 may be sorted into a "GOOD" list. However, the material layer patterns which were identified as failure patterns in operation S1012 may be mostly included in a "BAD" list and have a high probability to be detected as having hotspots in operation S1020.

Each of the lists may display a unique identifier (ID) of a material layer pattern formed on a wafer and a DV corresponding to the ID. When selecting a unique ID included in each list, a CD-SEM image of the material layer pattern corresponding to the selected ID may be displayed. A selection may be made by clicking an icon on a display screen. A location of a hotspot, a contour image, and a target layout image may be simultaneously displayed on the selected CD-SEM image.

When selecting an arbitrary unique ID included in the "GOOD" list, a CD-SEM image corresponding to the selected ID may be displayed. A contour image and a target layout image may be simultaneously displayed on the CD-SEM image.

When selecting an arbitrary unique ID included in the "VAGUE" list, a CD-SEM image corresponding to the selected ID may be displayed. A contour image and a target layout image may be simultaneously displayed on the CD-SEM image. Material layer patterns sorted into the "VAGUE" list may include a material layer pattern which is identified as requiring an additional review according to an engineer's, inspector's, or the like's check based on a shape of the material layer pattern.

When selecting an arbitrary unique ID included in the "BAD" list, a CD-SEM image corresponding to the selected ID may be displayed. Failure patterns, which are the bridge shown in FIG. 6 or 7, the EPE or the pinch shown in FIG. 8, or the like, are simultaneously displayed on the CD-SEM image as hotspots together with a contour image and a target layout image.

An engineer, inspector, or the like may mainly check a "VAGUE" or a "BAD" list rather than a "GOOD" list, which indicates material layer patterns not having hotspots, among the "GOOD," the "VAGUE," and the "BAD" lists. As the "BAD" list indicates a region highly likely of generating hotspots, a visual inspection should be performed by the engineer, inspector, or the like. Although the material layer patterns sorted in the "VAGUE" list are not clearly identified as having hotspots, the material layer patterns in the "VAGUE" list are regarded as having a potential hotspot region which may need to be visually inspected by the engineer, inspector, or the like.

In operation S1022, whether a review result of the CD-SEM image is "GOOD" may be checked.

When a result of the CD-SEM image review is "GOOD," the wafer proceeds to operation S1024. The "GOOD" result from the CD-SEM image review indicates that a hotspot is not shown on the wafer, or the hotspot is shown but is denoted as a minor (or, ignored) hotspot which may not affect a process.

For example, in operation S1022, all the CD-SEM images with respect to patterns sorted as "GOOD" patterns through sorting qualities of the material layer patterns in operation S1014 may be reviewed.

By reviewing all the CD-SEM images, although they were checked as a "GOOD" pattern in operation S1014, a pattern which needs a more accurate check or an optical proximity correction (OPC) correction may be found.

In operation S1024, a semiconductor device may be formed by performing a subsequent process with respect to the wafer checked as "GOOD."

When a material layer pattern on the wafer is a photoresist pattern, a process may include selectively etching an underlayer using the material layer pattern as a self-aligned etching mask.

When the underlayer is a conductive layer, a process may include selectively etching the underlayer by the material layer pattern as an etching mask, and forming a pattern which is a word line, a bit line, an interconnection line, or the like, serving as a transmission path for an electrical signal. The conductive layer may include a metal layer or polysilicon layer.

For example, when the underlayer is an insulating layer, a process may include forming an insulating pattern which insulates between adjacent conductive layers. The insulating layer may include an oxide layer or nitride layer.

According to a review result in operation S1022, when a review result from the CD-SEM image is not "GOOD," the wafer proceeds to operation S1026. The case in which the review result from the CD-SEM image is not "GOOD," indicates that a hotspot may exist on the wafer, and it denotes that the hotspot may negatively affect a process.

In operation S1026, the hotspot on the CD-SEM image may be next reviewed through a visual inspection by an engineer, inspector, or the like.

As the visual inspection is performed by the engineer, inspector, or the like with respect to the hotspot first detected through the computer review tool in operation S1020, a more detailed and aggressive response with respect to the detected hotspot may be considered.

In operation S1028, an OPC, which corrects a layout of the material layer pattern in which the hotspot may be generated, may be performed. The cause of the hotspot generation may be removed through the above OPC.

After performing the OPC with respect to the hotspot, the wafer returns to operation S1000, and may perform again a process which forms material layer patterns on the wafer.

In an exemplary embodiment of the inventive concept, when reviewing a CD-SEM image in operation S1020, a CD of material layer patterns which need a CD measurement may be measured in real-time. As the measured CD is displayed on the CD-SEM image as a reference mark 150 as shown in FIG. 6, convenience of a CD measurement operation may be increased.

In an exemplary embodiment of the inventive concept, a hotspot (e.g., a failure point) is first and automatically detected by calculating the DV from the area difference between the contour image and the target layout image of the material layer patterns formed on the wafer using the computer, and the first detected hotspot is displayed on the CD-SEM image.

Further, a selective and intensive visual inspection may be next performed by an engineer, inspector, or the like with respect to the hotspot (and the failure point such as the potential hotspot) displayed on the CD-SEM image first detected through the computer.

Thus, additional or an unnecessary review time spent to check a region in which a hotspot is not generated may be reduced. In this case an engineer, inspector, or the like can spend less time on such matters. Therefore, quick and accurate review and response (e.g., subsequent operations) with respect to the hotspot can be accomplished.

When considering a turn-around time (TAT), which is time spent on an entire wafer review and OPC, in a case in which a wafer review is performed according to a visual inspection by an engineer, inspector or the like, one to two days or more may be spent on a wafer review operation based on 5,000 chip regions. However, in an exemplary embodiment of the inventive concept in which a wafer review operation using a review tool in a computer and a wafer review operation by a visual inspection of an engineer, inspector, or the like are performed in parallel, the TAT may be completed within 6 to 12 hours.

For example, in the past it was inconvenient to measure a CD after loading a CD-SEM image through a separate computer program to measure the CD with respect to a pattern on a wafer.

However, in an exemplary embodiment of the inventive concept, since the CD is measured in real-time with respect to a desired pattern in a review process of the CD-SEM image to detect a hotspot on a wafer, convenience may be increased.

Further, in an exemplary embodiment of the inventive concept, a method, which displays a hotspot by automatically detecting through a two-dimensional CD-SEM image has been described, but the hotspot may be detected from a vertical cross-sectional structure through a three-dimensional CD-SEM image. When the hotspot is detected from the vertical cross-sectional structure through the three-dimensional CD-SEM image, a location of the hotspot may be calculated and detected using three-dimensional vertical coordinates (X, Y, Z) instead of two-dimensional planar coordinates, and may be displayed on the CD-SEM image.

Figure 9:
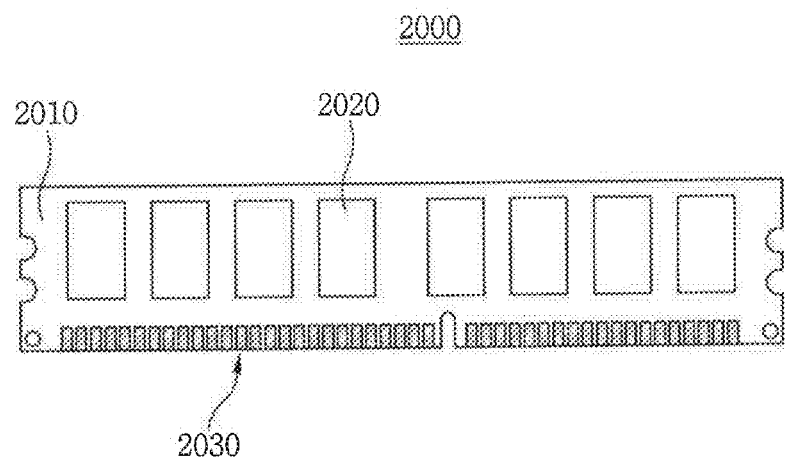
FIGS. 9 and 10 are views schematically illustrating semiconductor modules including a semiconductor device in accordance with an exemplary embodiment of the inventive concept.

FIG. 9 is a view schematically illustrating a semiconductor module 2000 including a semiconductor device manufactured in accordance with an exemplary embodiment of the inventive concept.

Referring to FIG. 9, the semiconductor module 2000 may include a memory module including a memory device. The semiconductor module 2000 may include a module substrate 2010, a plurality of semiconductor devices 2020 disposed on the module substrate 2010, and a plurality of terminals 2030. The terminals 2030 may include a conductive metal. The terminals 2030 may be electrically connected to the semiconductor devices 2020. The module substrate 2010 may include a memory module substrate. The module substrate 2010 may include a printed circuit board (PCB) or a wafer.

The semiconductor devices 2020 may include memory devices. The semiconductor devices 2020 may include dynamic random access memory (DRAM) devices. The semiconductor devices 2020 may include a semiconductor device in accordance with an exemplary embodiment of the inventive concept, or a semiconductor package including the semiconductor device.

Figure 10:
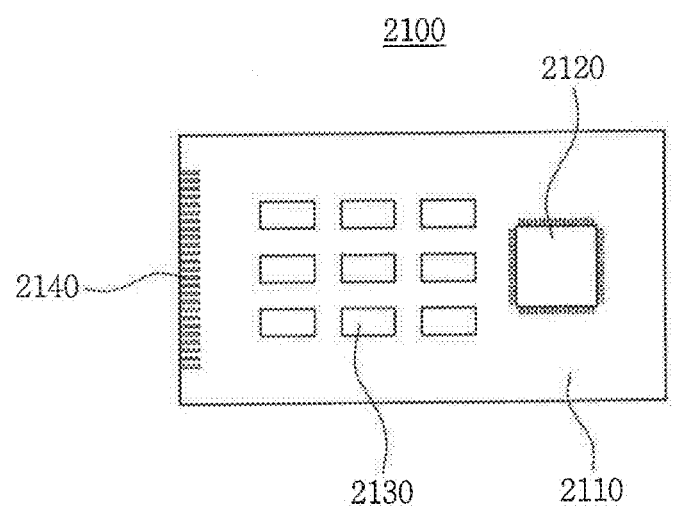

FIG. 10 is a view schematically illustrating a semiconductor module 2100 including a semiconductor device manufactured in accordance with an exemplary embodiment of the inventive concept.

Referring to FIG. 10, the semiconductor module 2100 may include a memory device 2130 formed on a module substrate 2110. The memory device 2130 may include a memory device such as a NAND flash memory, etc. The semiconductor module 2100 may include a semiconductor device 2120 mounted on the module substrate 2110. Input/output terminals 2140 may be disposed on at least one side of the module substrate 2110.

Figure 11:
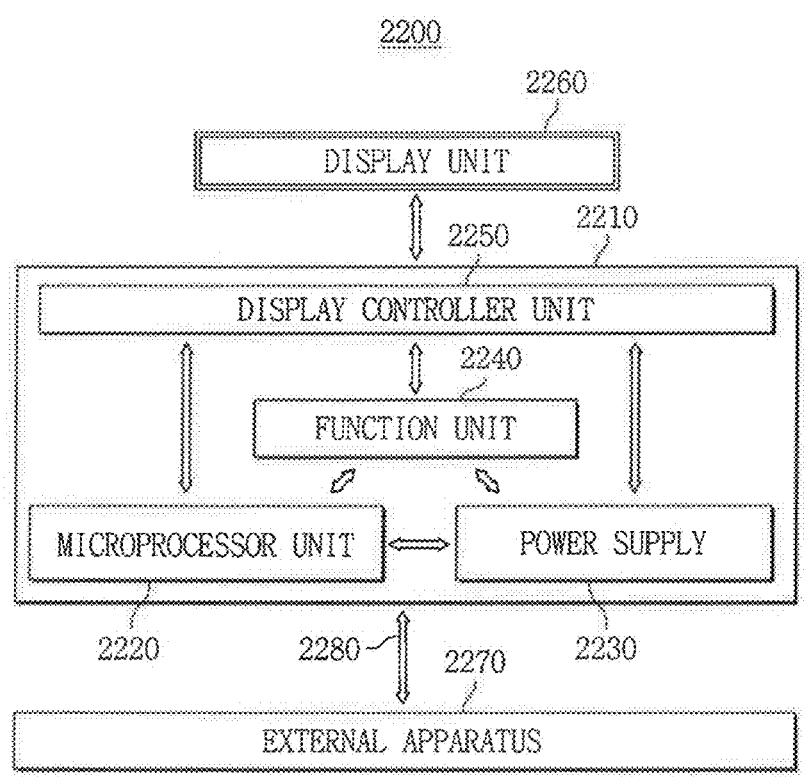
FIG. 11 is a block diagram illustrating an electronic system including a semiconductor device in accordance with an exemplary embodiment of the inventive concept.

FIG. 11 is a block diagram illustrating an electronic system 2200 including a semiconductor device in accordance with an embodiment of the inventive concept.

Referring to FIG. 11, the electronic system 2200 may include a body 2210. The body 2210 may include a microprocessor unit 2220, a power supply 2230, a function unit 2240, and/or a display controller unit 2250. The body 2210 may include a system board or motherboard including a PCB, etc.

The microprocessor unit 2220, the power supply 2230, the function unit 2240, and the display controller unit 2250 may be mounted or installed on the body 2210. A display unit 2260 may be disposed on an upper surface of the body 2210 or outside the body 2210. For example, the display unit 2260 may be disposed on a surface of the body 2210 and display an image processed by the display controller unit 2250. The power supply 2230 may receive a constant voltage from an external power source or the like, the voltage may be divided into various voltage levels, and the various voltages are supplied to the microprocessor unit 2220, the function unit 2240, the display controller unit 2250, etc. The microprocessor unit 2220 may receive a voltage from the power supply 2230, and control the function unit 2240 and the display unit 2260.

The function unit 2240 may perform various functions of electronic system 2200. For example, when the electronic system 2200 is a mobile electronic product such as a mobile phone, the function unit 2240 may include dialing, or various components capable of performing wireless communication functions such as video output to the display unit 2260, audio output to a speaker and/or the like in communication with an external apparatus. When a camera is included therein, it may serve as an image processor.

In an exemplary embodiment of the inventive concept, when the electronic system 2200 is connected to a memory card or the like to expand capacity, the function unit 2240 may be a memory card controller. The function unit 2240 may exchange a signal with an external apparatus 2270 through a wired or wireless communication unit 2280.

For example, when the electronic system 2200 requires a Universal Serial Bus (USB) or the like to expand functions, the function unit 2240 may serve as an interface controller.

Figure 12:
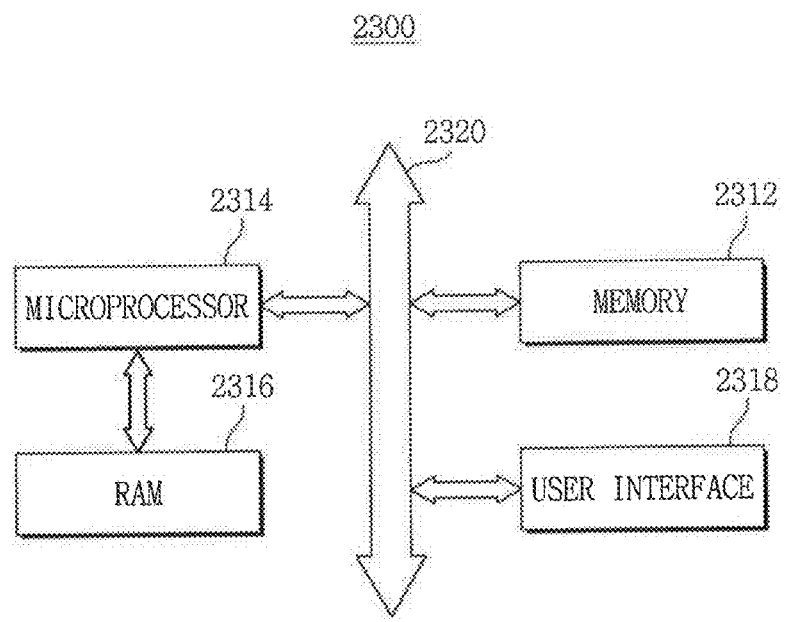
FIG. 12 is a block diagram schematically illustrating an electronic system including a semiconductor device in accordance with an exemplary embodiment of the inventive concept.

FIG. 12 is a block diagram schematically illustrating an electronic system 2300 including a semiconductor device in accordance with an embodiment of the inventive concept.

Referring to FIG. 12, the electronic system 2300 may include a semiconductor device in accordance with an exemplary embodiment of the inventive concept. The electronic system 2300 may be used for manufacturing a mobile device or computer. For example, the electronic system 2300 may include a user interface 2318 which performs data communication using a memory system 2312, a microprocessor 2314, a RAM 2316, and a bus 2320. The microprocessor 2314 may program and control the electronic system 2300. The RAM 2316 may be used for an operational memory of the microprocessor 2314. The microprocessor 2314, RAM 2316, and/or other components may be assembled in a single package. The memory system 2312 may include the semiconductor device according to an exemplary embodiments of the inventive concept, or a semiconductor package including the semiconductor device.

The user interface 2318 may be used for data input to the electronic system 2300 or data output from the electronic system 2300. The memory system 2312 may store operational codes of the microprocessor 2314, data processed by the microprocessor 2314, or external input data. The memory system 2312 may include a controller and a memory.

Figure 13:
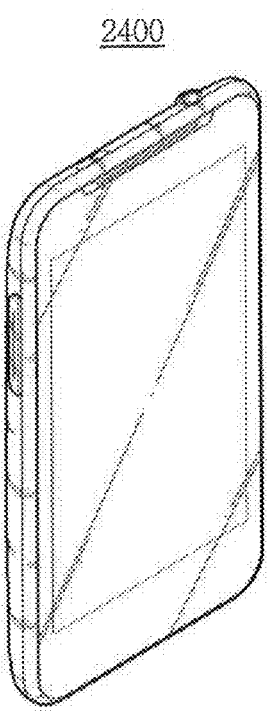
FIG. 13 is a view schematically illustrating a wireless mobile phone including a semiconductor device in accordance with an exemplary embodiment of the inventive concept.

FIG. 13 is a view schematically illustrating a mobile wireless phone 2400 including a semiconductor device in accordance with an exemplary embodiment of the inventive concept. The mobile wireless phone 2400 may include a semiconductor device in accordance with an exemplary embodiment of the inventive concept. The mobile wireless phone 2400 may be understood as a tablet personal computer (PC). For example, the semiconductor device in accordance with an exemplary embodiment of the inventive concept may be used for a portable computer such as a notebook, an mpeg-1 audio layer-3 (MP3) player, an MP4 player, a navigation device, a solid state disk (SSD), a table computer, a vehicle, and home appliances in addition to a tablet PC.

By the pattern analysis method of the semiconductor device in accordance an exemplary the embodiment of the inventive concept, hotspots are detected through an area difference between a contour image and a target layout image extracted from a CD-SEM image of a pattern formed on a wafer, and the detected hotspots are displayed on the CD-SEM image for an engineer, inspector, or the like.

Thus, time that an engineer, inspector, or the like, spends on a visual inspection of a wafer may be reduced. Therefore, reliability of a semiconductor device and productivity of an engineer, inspector, or the like, may be increased.

Further, during a review of the hotspots using the CD-SEM image, a CD is measured in real-time with respect to a desired pattern. Thus, convenience of a CD measurement operation may be increased.

While the inventive concept have been described with reference to exemplary embodiments thereof, those skilled in the art will readily appreciate that many modifications may be made therein without departing from the inventive concept as defined by the claims.

What is claimed is:

1. A pattern analysis method of a semiconductor device, comprising:
    extracting a contour image of material layer patterns formed on a wafer;
    calculating an individual density value (DV) representing an area difference between the contour image and a target layout image;
    scoring the material layer patterns on the wafer using the individual DV;
    identifying a failure pattern among the scored material layer patterns;
    calculating coordinates of the identified failure pattern and displaying the coordinates on a critical dimension-scanning electron microscopy (CD-SEM) image;
    inputting a reference DV in a computer and automatically sorting the material layer patterns into material layer patterns having a hotspot and material layer patterns not having a hotspot; and
    reviewing the sorted material layer patterns having the hotspot,
    wherein the inputting of the reference DV and the automatically sorting of the material layer patterns on the wafer into those having a hotspot and those not having a hotspot includes:
    inputting a DV data file, a pinch/bridge/Edge Placement Error (EPE) data file, an image data file, and a threshold value for sorting the DV into a review tool installed in the computer; and
    sorting the material layer patterns on the wafer into a "BAD" list which includes material layer patterns having a hotspot, a "GOOD" list which includes material layer patterns not having a hotspot, and a "VAGUE" list which includes material layer patterns not having a hotspot, according to the input DV data file, pinch/bridge/EPE data file, image data file, and threshold value for sorting the DV.

2. The pattern analysis method of claim 1, wherein the contour image is extracted with respect to end regions of the material layer patterns.

3. The pattern analysis method of claim 1, wherein the target layout image includes an original design target layout, a smoothing target layout, or a simulation target layout.

4. The pattern analysis method of claim 1, wherein the individual DV is calculated through the following Equation:

$$DV = \frac{[\text{Area}(SEMunit) - \text{Area}(SEMsilhouette \cap Target)] + [\text{Area}(Target) - \text{area}(SEMsilhouette \cap Target)]}{\text{Area}(SEMunit)},$$

wherein the Area(SEMunit) is an area of a region of the wafer illustrated in the CD-SEM image, the Area(SEMsilhouette) is an area of the Area(SEMunit) occupied by the contour image of the material layer patterns, and the Area(Target) is an area of the Area(SEMunit) occupied by the target layout image.

5. The pattern analysis method of claim 1, wherein a failure pattern is identified when an area matched between the contour image and the target layout image is less than a predetermined threshold.

6. The pattern analysis method of claim 1, wherein the identified failure pattern includes a "bridge," a "pinch," or an "Edge Placement Error (EPE)".

7. The pattern analysis method of claim 1, wherein each of the lists includes a unique identifier (ID) of each material layer pattern and a DV corresponding to the ID.

8. The pattern analysis method of claim 7, wherein when selecting an ID included in each of the lists, a CD-SEM image of a material layer pattern corresponding to the selected ID is displayed, and a location of the hotspot, the contour image, and the target layout image of the selected ID are simultaneously displayed on the corresponding CD-SEM image.

9. The pattern analysis method of claim 1, wherein the material layer patterns sorted as having a hotspot include material layer patterns having an actual hotspot and material layer patterns having a potential hotspot in which a failure is able to be generated.

10. The pattern analysis method of claim 9, wherein the reviewing includes visually reviewing the material layer patterns having the actual hotspot and the material layer patterns having the potential hotspot.

11. The pattern analysis method of claim 1, wherein a critical dimension (CD) value of each material layer pattern displayed on the CD-SEM image is measured and displayed in real-time.

12. A pattern analysis method of a semiconductor device, comprising:
    calculating a density value (DV) representing an area difference between a contour image of the material layer patterns formed on a wafer and a target layout image, using a computer;
    inputting a reference DV to be compared with the calculated DV of the material layer patterns and automatically detecting a hotspot of the material layer patterns, using the computer;
    displaying the detected hotspot on a critical dimension-scanning electron microscopy (CD-SEM) image, using the computer; and
    performing a visual inspection of the displayed hotspot on the CD-SEM image,
    wherein the calculated DV of the material layer patterns is determined through the following Equation:

$$DV = \frac{[\text{Area}(SEMunit) - \text{Area}(SEMsilhouette \cap Target)] + [\text{Area}(Target) - \text{area}(SEMsilhouette \cap Target)]}{\text{Area}(SEMunit)},$$

wherein the Area(SEMunit) is an area of a region of the wafer illustrated in the CD-SEM image, the Area(SEMsilhouette) is an area of the Area(SEMunit) occupied by the contour image of the material layer patterns, and the Area(Target) is an area of the Area(SEMunit) occupied by the target layout image.

13. The pattern analysis method of claim 12, wherein an optical proximity correction (OPC) is performed after performing the visual inspection.

14. The pattern analysis method of claim 12, wherein the CD-SEM image includes a two-dimensional CD-SEM image or a three-dimensional CD-SEM image.

15. The pattern analysis method of claim 12, wherein the hotspot is a failure point.

16. A pattern analysis method of a semiconductor device, comprising:
    obtaining a contour image of material layer patterns on a wafer;
    overlapping the contour image and a target layout image;
    obtaining a density value (DV) representing an area difference between the contour image and the target layout image;
    scoring the material layer patterns based on the DV;
    sorting the scored material layer patterns into material layer patterns that include a failure pattern, which is indicative of a hotspot, and material layer patterns that do not include the failure pattern;
    calculating coordinates on the wafer for the failure pattern and displaying the calculated coordinates on an image;
    automatically detecting a hotspot by applying a reference DV to the material layer patterns that include the failure pattern; and
    reviewing the automatically detected hotspot,
    wherein the DV is calculated through the following Equation:

$$DV = \frac{[\text{Area}(\textit{SEMunit}) - \text{Area}(\textit{SEMsilhouette} \cap \text{Target})] + [\text{Area}(\text{Target}) - \text{area}(\textit{SEMsilhouette} \cap \text{Target})]}{\text{Area}(\textit{SEMunit})},$$

wherein the Area(SEMunit) is an area of a region of the wafer illustrated in a critical dimension-scanning electron microscopy (CD-SEM) image, the Area(SEMsilhouette) is an area of the Area(SEMunit) occupied by the contour image of the material layer patterns, and the Area(Target) is an area of the Area(SEMunit) occupied by the target layout image.

17. The pattern analysis method of claim 16, wherein the image includes a two-dimensional critical dimension scanning electron microscopy (CD-SEM image or a three-dimensional CD-SEM image.

18. The pattern analysis method of claim 16, wherein an optical proximity correction (OPC) is performed after reviewing the automatically detected hotspot.

* * * * *